United States Patent [19]

Schwartz

[11] Patent Number: 5,314,824
[45] Date of Patent: May 24, 1994

[54] METHOD OF SETTING UP A FLOW CYTOMETER

[75] Inventor: Abraham Schwartz, Hato Rey, P.R.

[73] Assignee: Caribbean Microparticles Corporation, Hato Rey, P.R.

[21] Appl. No.: 966,937

[22] Filed: Oct. 27, 1992

Related U.S. Application Data

[63] Continuation-in-part of Ser. No. 671,198, Mar. 18, 1991, abandoned, which is a continuation-in-part of Ser. No. 620,530, Nov. 21, 1990, Pat. No. 5,089,416, which is a continuation-in-part of Ser. No. 516,056, Apr. 27, 1990, Pat. No. 5,084,394, which is a continuation-in-part of Ser. No. 128,786, Dec. 4, 1987, Pat. No. 4,857,451, which is a continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.[5] .......................................... G01N 33/547
[52] U.S. Cl. .......................................... 436/10; 436/8; 436/63; 436/800; 252/408.1; 250/461.2; 356/36
[58] Field of Search .......................... 252/301.35, 408.1; 250/461.2; 356/36; 424/3; 435/7; 436/8, 10, 19, 800, 63, 174; 427/213.3, 213.36

[56] References Cited

U.S. PATENT DOCUMENTS

| | | | |
|---|---|---|---|
| 4,035,316 | 7/1977 | Yen et al. | 260/2.5 B |
| 4,157,323 | 6/1979 | Yen et al. | 260/29.7 |
| 4,162,282 | 7/1979 | Fulwyler et al. | 264/9 |
| 4,247,434 | 1/1981 | Vanderhoff et al. | 260/29.6 |
| 4,254,096 | 3/1981 | Monthony et al. | 424/8 |
| 4,438,239 | 3/1984 | Rembaum et al. | 525/54.1 |
| 4,511,662 | 4/1985 | Baran et al. | 436/513 |
| 4,552,633 | 11/1985 | Kumakura et al. | 204/159.21 |
| 4,605,630 | 8/1986 | Kung et al. | 436/511 |
| 4,609,689 | 9/1986 | Schwartz et al. | 523/202 |
| 4,656,144 | 4/1987 | Hosaka et al. | 436/534 |
| 4,665,020 | 5/1987 | Saunders | 435/7 |
| 4,694,035 | 9/1987 | Kasai et al. | 524/458 |
| 4,698,262 | 10/1987 | Schwartz et al. | 428/402 |
| 4,699,826 | 10/1987 | Schwartz et al. | 428/402 |
| 4,699,828 | 10/1987 | Schwartz et al. | 428/402 |
| 4,714,682 | 12/1987 | Schwartz | 436/10 |
| 4,751,188 | 6/1988 | Valet | 436/63 |
| 4,767,206 | 8/1988 | Schwartz | 356/73 |
| 4,774,189 | 9/1988 | Schwartz | 436/10 |
| 4,828,984 | 5/1989 | Schwartz | 435/7 |
| 4,857,451 | 8/1989 | Schwartz | 435/7 |
| 4,867,908 | 9/1989 | Recktenwald et al. | 252/408.1 |
| 4,868,126 | 9/1989 | Schwartz | 436/10 |
| 4,918,004 | 4/1990 | Schwartz | 435/7 |

*Primary Examiner*—James C. Housel
*Assistant Examiner*—David Redding
*Attorney, Agent, or Firm*—Olive & Olive

[57] ABSTRACT

A method of setting up a flow cytometer using microbeads fluorescing at a plurality of wavelengths, control cells for each of said wavelengths, certified blank microbeads. The blank microbeads are run and the PMT voltages are adjusted so that the blank microbeads are on scale on the flow cytometer. The control cells are run and the photomultiplier tube voltages are adjusted so that the single population falls in selected channels. The fluorescent microbeads are run on the flow cytometer and the Target Channels for the flow cytometer are determined.

11 Claims, 2 Drawing Sheets

5,314,824

METHOD OF SETTING UP A FLOW CYTOMETER

CROSS-REFERENCE TO RELATED APPLICATIONS

This application is a continuation-in-part of co-pending U.S. patent application Ser. No. 07/671,198, filed Mar. 18, 1991, now abandoned, which is a continuation-in-part of U.S. patent application Ser. No. 07/620,530, filed Nov. 21, 1990 and issued Feb. 18, 1992 as U.S. Pat. No. 5,089,416, and U.S. patent application Ser. No. 07/516,056, filed Apr. 27, 1990 and issued Jan. 28, 1992 as U.S Pat. No. 5,084,394, each of which is a continuation-in-part of U.S. patent application Ser. No. 07/128,786, filed Dec. 4, 1987 and issued as U.S. Pat. No. 4,857,451 on Aug. 15, 1989, which is a continuation-in-part of U.S. patent application Ser. No. 06/805,654, filed Dec. 11, 1985 and issued as U.S. Pat. No. 4,774,189 on Sep. 27, 1988, which is a continuation-in-part of U.S. patent application Ser. No. 06/685,464, filed Dec. 24, 1984 and issued as U.S. Pat. No. 4,767,206 on Aug. 30, 1988. The disclosure of the above co-pending patent application and the above issued patents is hereby incorporated herein.

BACKGROUND OF THE INVENTION

1. Field of the Invention

This invention relates to flow cytometers, and in particular, relates to a method of standardization of flow cytometers.

2. Description of the Related Art

Standardization of flow cytometers is critical and it is important that instrument performance be reproducible and that results obtained on a particular instrument be comparable from day to day and with results obtained on other instruments.

Previous inventions have utilized a variety of flow cytometer standardization methods. For example, U.S. Pat. No. 5,093,234 discloses a kit containing microbead populations, each of which has the same dye but different fluorescence levels, and on which the microbeads have the same underlying fluorescence characteristics as the sample to be run on the flow cytometer. This kit allows aligning, compensating and/or calibration of a flow cytometer using microbead standards so that data is reproducible from instrument to instrument and from one time to another time on the same instrument but microbead standards do not approach the accuracy of cell standards. The disclosure of this patent and all other patents and patent applications referred to herein is hereby incorporated herein by reference.

U.S. Pat. No. 5,073,497 discloses microbead reference standards, called QC3 TM beads, for adjustment of a flow cytometer for subsequent measurement of a selected cell or particle sample labeled with two or more dyes. The microbeads are labeled with the same dyes and have substantially the same size which is about the size of the sample. These standards allow adjustment of a flow cytometer for analysis of selected samples which may have multiple fluorescence labels.

In co-pending patent application U.S. Ser. No. 07/671,198, an automated system, QUICK-CAL®, is provided for calibrating and determining performance of a flow cytometer. In this method, statistical data is generated, including the fluorescence threshold and the MESF-slope of the regression line of the plot of histogram channel vs. MESF of standard microbead populations as a function of peak channel number. MESF units are measures of fluorescence intensity expressed as molecules of equivalent soluble fluorochromes. As presented in co-pending U.S. application Ser. No. 07/671,198, the following formula expresses the relationship between MESF value and the slope of the plot of histogram channel vs. MESF as follows: MESF=exp((channel+a constant)/slope). The values obtained are used to show instrument stability. A CLEANSWEEP TM gating function sets a numerical threshold and eliminates populations and events which fall below that level. This invention allows rapid, automatic determination of the slopes, fluorescence thresholds (noise levels), linearities, and Target Channels.

The noise level of a flow cytometer, which is the sum of the optical and electronic noise of the instrument, is important in instrument performance. This noise level varies between flow cytometers. On a particular flow cytometer, the noise level varies with changing ambient conditions, with the type of sample being analyzed, with electrical supply and with stability of flow cytometer fluidics. It is an object of this invention to provide a method which allows flow cytometers to be compared over time and with other flow cytometers regardless of noise level. It is another object of this invention to provide a method for setting up a flow cytometer for determination and qualitative evaluation of the noise level of a flow cytometer.

Prior methods of setting and standardizing compensation of flow cytometers usually place unstained cells in the corner of what is discussed herein as the Window of Analysis, resulting in non-uniform compensation across the intensity ranges being used. It is an object of this invention to provide a method resulting in uniform compensation at any intensity range used.

Non-fluorescent microbeads or "blank" microbeads are used to determine fluorescence threshold of a flow cytometer. The blank microbeads are run on the flow cytometer at the same flow cytometer setting where a selected auto fluorescent sample has observable auto fluorescence, and the peak channel position is used as a fluorescence threshold (U.S. Pat. No. 5,089,416).

Utilizing blank microbeads to set up flow cytometers, it has been found by the inventor herein that with a substantial percentage of flow cytometers with compensation circuits as originally set up by the manufacturers, there is a difference in the relative fluorescence of the blank microbeads and unstained cells depending on whether the compensation circuits are turned on or off. When the compensation circuits are not set up correctly, blank microbeads have a lower fluorescence than unstained cells when the compensation circuits are off, but a higher fluorescence than unstained cells when the compensation circuits are on. Flow cytometer operators thus risk losing data on low fluorescence samples on these flow cytometers. It is therefore an object of this invention to provide a method of setting up a flow cytometer which allows determination of whether the compensation circuits have been set up correctly.

It is a further object of this invention to provide a method for setting up a flow cytometer which allows fluorescence compensation to be set and to be uniform across the range of fluorescence intensity used.

It is a further object of this invention a method for setting up a flow cytometer to provide verification of sample preparation and reagent stability.

It is a further object of this invention a method for setting up a flow cytometer to ensure comparability of instrument performance from day to day and from instrument to instrument.

Other objects and advantages will be more fully apparent from the following disclosure and appended claims.

SUMMARY OF THE INVENTION

This method for standardizing flow cytometers for use in studying fluorescently labeled cells, comprises utilizing blank and labeled microbeads along with stained control cells. The method of setting up a flow cytometer uses microbeads fluorescing at a plurality of specific wavelengths, control cells labeled with fluorochromes at each of said wavelengths, and CERTIFIED BLANK TM microbeads. The invention herein preferably provides a method for standardizing a flow cytometer, for example, by using QC3 TM microbeads, which are microbeads which are surface labeled with both fluorescein isothiocyanate (FITC) and phycoerythrin (PE), and the CERTIFIED BLANK TM microbeads.

In the method of the invention, blank microbeads are run on the flow cytometer and the PMT voltages are adjusted so that the blank microbeads are on scale on the flow cytometer. The control cells are run and the photomultiplier tube voltages are adjusted so that the singlet population falls in selected channels. The fluorescent microbeads are run on the flow cytometer and the Target Channels for the flow cytometer are determined.

Other aspects and features of the invention will be more fully apparent from the following disclosure and appended claims.

DETAILED DESCRIPTION OF THE INVENTION AND PREFERRED EMBODIMENTS THEREOF

Figure 1:
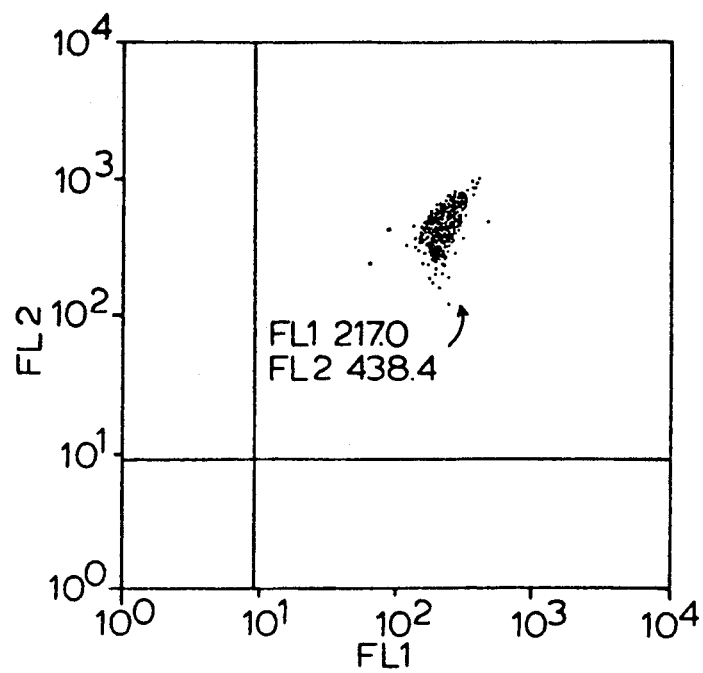
FIG. 1 is a dot plot of the green fluorescence channel FL1 versus the red fluorescence channel FL2 of a flow cytometer prior to compensation when QC3 TM microbeads are in their Initial Target Channels.

The present invention provides a method of setting up a flow cytometer so that it may be used with fluorescently stained cells. This method includes determination of Target Channels as discussed herein, and in particular, includes determination of initial Target Channels and instrument-specific Target Channels, and subsequent use of the instrument-specific target channel information. As a part of the instrument set-up, the fluorescence intensity of unstained cells is compared to the fluorescence intensity of blank microbeads with the compensations circuits off and then on as discussed below.

The method of the invention for setting up a flow cytometer allows determination and qualitative evaluation of the noise level of a flow cytometer relative to a particular assay on a particular type of cells. The invention utilizes a combination of microbead standards which the operator of a flow cytometer can use in conjunction with stained control samples to set PMT voltages and compensation circuits consistently and qualitatively evaluate the noise level of the instrument relative to a particular assay.

In particular, the invention provides a method of setting up a flow cytometer having photomultiplier tubes (PMTs) which has adjustable voltages and a plurality of fluorescent channels at each of two or more selected wavelengths for use with fluorescent cells. The method comprises:

(a) providing blank microbeads;

(b) providing a set of control cell populations for each of said wavelengths, each control cell population being singly labeled with a fluorescent compound which fluoresces at one of said wavelengths;

(c) providing a population of microbeads fluorescing at said wavelengths;

(d) running the said blank microbeads on said flow cytometer and adjusting the PMT voltages so that the blank microbeads are on scale on the flow cytometer;

(e) running said control cell populations for each said wavelengths on said flow cytometer and gating the control cell population to yield singlet cell populations;

(f) adjusting the compensation so that the singlet cell populations fall orthogonally to unstained cells in secondary fluorescence channels; and (g) running said population of microbeads fluorescing at said wavelengths and determining Target Channels for the flow cytometer.

Preferably the blank microbeads are CERTIFIED BLANK TM microbeads, which are defined herein as unlabeled microbead standards which have a fluorescence intensity less than the auto fluorescence intensity of unstained whole blood lysed human peripheral lymphocytes in all fluorescence channels. The word "certified" is added to distinguish these blank microbeads from other blank microbeads which have no measurable fluorescence using less rigorous or less well-defined measurements.

The cells with which the CERTIFIED BLANK TM microbeads are compared are human peripheral lymphocytes for use of the microbead with lymphocyte assays. The cells used may be other types of cell so long as the unstained cells used are the same kind of cells as the cells being analyzed.

CERTIFIED BLANK TM microbeads are used to determine and qualitatively evaluate noise level of a flow cytometer. If the CERTIFIED BLANK TM microbeads fall in a lower channel than the unstained cells, the instrument noise will not interfere with immunotyping assays using fluorescently labeled cells.

As the fluorescent microbeads, the invention preferably utilizes QC3 TM microbeads which are surface labeled with both fluorescein (FITC) and phycoerythrin (PE) according to U.S. Pat. No. 5,073,497, the disclosure of which is incorporated herein. Such labeling ensures that the QC3 TM microbeads maintain the same spectral properties as cells labeled with the same fluorochromes. Instead of QC3 TM microbeads, QC4 TM microbeads may be used, which are labeled, in addition to PE and FITC, with a third dye such as PE tandemly conjugated with a TEXAS RED TM, CY5 (CY5 is a cyanine dye with five carbon spacers between aromatic rings; when conjugated with phycoerythrin, CY5 is sold as TRI-COLOR TM by Catalog, Inc.) dye, or (PerCP) peridinin chlorophyll protein. Thus, whenever "QC3 TM" microbeads are referred to herein, QC4 TM or other analogously labeled microbeads may be used.

The Target Channels which are determined in the invention are fixed reference channels in the Windows of Analysis. Windows of Analysis are defined herein as the range covered by the histogram channels, for example, 256 or 1024 linear channels or 3 or 4 decade relative linear channels, of the various parameters of a flow cytometer, each Window of Analysis being visualized as a window on a 2-dimensional histogram (dot plot) or the scale on a one-dimensional histogram as appropriate for the particular flow cytometer.

The invention provides a method of setting the fluorescence compensation as follows: the PMTs are set so that the CERTIFIED BLANK TM microbeads are on scale. The fluorescence compensation circuits are then set by gating the population of control cells labeled with antibodies, which are preferably representative of the samples and antibodies to be used in the assay, and adjusting the compensation circuits so that the compensation lines (line going from the mean of the noise level or zero fluorescence to the mean of the cell population in the secondary channels) are parallel with the axes of the Window of Analysis. Thus, for example, if FITC and PE are the fluorescence labels used, FITC-labeled cells have the same fluorescence intensity in the PE channel as unstained cells.

Placing the CERTIFIED BLANK TM microbeads on scale keeps the stained and unstained cells away from the axes of the plot of FL1 vs. FL2 so it is easier to see if the cell population is over-compensated. Using the CERTIFIED BLANK TM microbeads according to the invention brings the noise level on scale and results in uniform compensation. Compensation is very dependent on both the FL1 and FL2 PMT settings across the intensity range of the Window of Analysis. Utilizing the invention herein, if the Target Channels and the slopes of the calibration curves of the FL1 and FL2 channels are the same on two different instruments or on the same instrument at two different times, the instruments have been adjusted to that they have the same Window of Analysis.

The channel where the CERTIFIED BLANK TM microbeads fall also approximates the pivot point for compensation purposes. The pivot point is defined herein as the point, for example, when FL1 is plotted vs. FL2, where zero fluorescence occurs and is the point around which the line of compensation rotates. The compensation lines should be parallel to the axes of the Window of Analysis to properly set the compensation for the entire intensity range. This means that the fluorescence of single-labeled cells should have the same fluorescence intensity in their secondary fluorescence channels as the unstained cells.

After the initial PMT voltages and compensation circuits are set the QC3 TM microbeads are used to set the Instrument-Specific Target Channels in the various parameters, such as forward angle light scatter (FALS), right angle light scatter (RALS), FL1 and FL2, to establish consistent Windows of Analysis. Adjustment of the PMT or gain settings repositions the Window of Analysis relative to scatter and fluorescent signals.

If the QC3 TM reference standards are always placed in the same Target Channels, the Windows of Analysis are comparable from day to day. If the instrument setting required to place the QC3 TM microbeads in the Target Channels changes, the instrument is not consistent, however, the resulting Window of Analysis will be consistent.

When the instrument is used again using the initial PMT and compensation settings, the QC3 TM microbeads should fall in their respective Instrument-Specific Target Channels, establishing the same Window of Analysis. If they do not fall in the same Target Channels, the PMTs may be adjusted, which may require adjustment of the compensation circuits. It is important that the control cells appear in the same positions in the Window of Analysis and are properly compensated.

Placing the QC3 TM microbeads in the same Initial Target Channels on different instruments which have the same amplifier range sets the same Window of Analysis for each of the instruments, which in turn positions the cell populations in the same areas of the Windows of Analysis of the two instruments.

Both the QC3 TM microbeads and the CERTIFIED BLANK TM microbeads used in the invention are preferably the same size as lymphocytes (7–9 u in diameter). The invention may be used by providing persons using one or more flow cytometers the CERTIFIED BLANK TM microbeads and QC3 TM beads, along with a table of Initial Target Channels which have been previously determined by running aliquots of the QC3 TM beads.

In the preferred embodiment of the invention, the method of the invention allow a flow cytometer of a selected model to be set up using initial Target Channels to determine instrument specific Target Channels. The embodiment of the method comprises:

(a) determining Initial Target Channels by:
  (i) providing blank microbeads;
  (ii) providing a set of control cell populations for each of said wavelengths, each control cell population being singly labeled with a fluorescent compound which fluoresces at one of said wavelengths;
  (iii) providing a population of microbeads fluorescing at said wavelengths;
  (iv) running said blank microbeads on said flow that the blank microbeads are on scale on the flow cytometer.
  (v) running the control cell populations for each of said wavelengths on said flow cytometer and gating the control cell population to yield singlet cell populations;
  (vi) adjusting the compensation so that the singlet cell populations fall orthogonally to unstained cells in secondary fluorescence channels;
  (vii) turning the compensation circuit off;
  (viii) running said population of microbeads fluorescing at said wavelengths and determining Initial Target Channels for the flow cytometer; and
  (ix) calculating equivalent Initial Target Channels for flow cytometers which have different amplifiers and scales;

(b) determining Instrument Specific Target Channels by:
  (i) running said population of microbeads fluorescing at said wavelengths with the compensation off and adjusting the PMT collages to place the fluorescing microbeads in said Initial Target Channels;
  (ii) running the control cell populations for each of said wavelengths on said flow cytometer and gating the control cell population to yield singlet cell populations;

(iii) adjusting the compensation so that the singlet cell populations fall orthogonally to unstained cells in secondary fluorescence channels; and (iv) running said population of microbeads fluorescing at said wavelengths and determining the Instrument Specific Target Channels; and (c) subsequently using the Instrument Specific Target Channels by:

(i) adjusting PMT and compensation settings to those determined in section (b);

(ii) running said population of microbeads fluorescing at said wavelengths and determining if said microbeads fall in said Instrument Specific Target Channels and thus if said instrument is performing as determined previously;

(iii) running the control cell populations for each of said wavelengths on said flow cytometer, gating the control cell population, and determining if the singlet cell populations fall in the same positions as previously and thus indicating said cells, or reagents or preparation are unchanged; and (iv) running said blank microbeads on said flow cytometer and determining if the blank microbeads have a lower fluorescence than the unstained cells and thus that the flow cytometer noise level will not interfere with the assay.

Initial Target Channels for the selected flow cytometer are preferably determined for the QC3 TM microbeads by the microbead manufacturer or provider or other person having access to the microbeads before distribution to end-users of the microbeads, however, the user may determine the Initial Target Channels by the above method. These initial Target Channels, as is discussed in more detail below, are used as the starting point for the microbead end-user, on any of the various flow cytometers available.

Before setting the initial Target Channels, the microbead provider runs the CERTIFIED BLANK TM microbeads and adjusts the PMTs so that the CERTIFIED BLANK TM microbeads, and thus the noise level, are on scale. Then, the stained cells of the appropriate cell type to be used later are run and the compensation is adjusted such that the cells are orthogonal in the secondary channel.

The microbead provider then turns off the compensation settings of the flow cytometer, runs the QC3 TM microbeads on the flow cytometer and determines the Initial Target Channels, or the channels of maximum fluorescence, for each fluorescence channel. Because individual flow cytometer compensation is so different between flow cytometers, placing the QC3 TM microbeads in the Initial Target Channels with the compensation turned off allows transferability of Initial Target Channels from instrument to instrument. The provider can calculate initial Target Channels for various models of flow cytometer by conversion of linear channels to relative channels if required. For example, a linear channel of a 1024, linear scale flow cytometer may be converted to a 4-decade log scale (relative linear channels) by taking 10 to the power of the channel divided by 256, for example, $10^{1024 \div 256}$.

Using Table 1 below or similar flow cytometer information, the QC3 TM microbeads and the initial Target Channel information, the end-user of the QC3 TM microbeads can determine what the instrument Target Channels should be for the end-user's particular flow cytometer. The end-user runs the fluorescently-labeled microbeads, such as QC3 TM microbeads (with the compensation off) and places them in the Initial Target Channels by adjusting the PMTs.

The end-user then turns on the compensation and runs control cells, such as CD4 and CD8 cells and adjusts the compensation so that the cells are orthogonal in the secondary channels. The end-user finally runs then QC3 TM microbeads and records the instrument specific Target Channels, which are likely to be different from the initial Target Channels due to instrument differences.

Running unknown cells on different flow cytometers which have been set-up as described above yields essentially identical results on the different instruments, and the FL1 vs. FL2 dot plot is repeatable between instruments and on the same instrument.

The features and advantages of the present invention will be more clearly understood by reference to the following examples, which are not to be construed as limiting the invention.

EXAMPLES

EXAMPLE 1

Demonstration of setting comparable Windows of Analysis with spectrally matching reference standards A FACScan flow cytometer (Becton Dickinson Immunocytometry Systems) is set-up by adjusting the PMT voltages such that whole human peripheral lysed blood labeled with CD4-PE and CD8-FITC antibodies, obtained from Becton Dickinson (Mountain View, Calif.) or Coulter Electronics (Hialeah, Fla.) appear in a select place in the Window of Analysis. QC3 TM microbeads (Flow Cytometry Standards Corporation, Research Triangle Park, N.C.) labeled with FITC and PE are used as a reference standard and the FL1 and FL2 Target Channels are determined on the FACScan flow cytometer for the Windows of Analysis. Then the QC3 TM microbeads are run on two other flow cytometers, a Profile II flow cytometer (Coulter Electronics Inc., Hialeah, Fla.) and a CytoronAbsolute flow cytometer (Ortho Diagnostic Systems, Inc., Raritan, N.J.), and are placed in the same Target Channels as they are on the FACScan flow cytometer by adjusting the PMT voltage of the particular flow cytometer. The same CD4-PE/CD8-FITC labeled cells are run on each of these instruments and are found to be in the same place in the Windows of Analysis on the two instruments because the Target Channel location of the cells matches.

EXAMPLE 2

Demonstration of setting non-comparable Windows of Analysis with reference standards which do not spectrally match the samples.

A second reference standard, DNA CHECK TM microbeads obtained from Coulter Electronics labeled with a dye other than FITC and PE, is run on the same FACScan flow cytometer and at the same instrument settings as in Example 1 and the Target Channels are determined. When the DNA CHECK TM microbeads are placed in the same Target Channels on the two other flow cytometers used in Example 1 as they have on the FACScan instrument, the same CD4-PE/CD8-FITC labeled cells used in Example 1 appear in different places in the Windows of Analysis of the three instruments.

EXAMPLE 3

Demonstration of blank microbeads being the pivot point for compensation

A mixture of four populations of different intensity FITC-labeled microbeads, four populations of different intensity PE-labeled microbeads and blank microbeads are run on a FACScan flow cytometer. The FL1 and FL2 PMTs are adjusted to place the blank microbeads in the lower left corner of the Window of Analysis. The compensation circuits are adjusted so that the mid-range intensity FITC and PE microbead populations are the same intensities in the FL2 and FL1, respectively, as the blank microbeads. The other FITC and PE microbead populations are found to be correctly compensated across their entire intensity ranges.

EXAMPLE 4

Demonstration that the compensation is not set correctly across the intensity range when the pivot point is off scale Whole lysed peripheral human blood is stained in three tubes with CD2-FITC, CD4-FITC and CD8-FITC, which have increasing intensity of fluorescence, respectively. The unstained lymphocyte population is placed in the corner of a FL1 and FL2 Window of Analysis and the compensation is adjusted for the mid-intensity stained CD4-FITC lymphocytes such that they have the same fluorescence in the FL2 channels as the unstained population. When the high-intensity CD8-FITC stained lymphocytes are run at the same instrument settings, they are found to be under-compensated. When the low-intensity CD2-FIT lymphocytes are run, they are found to be over-compensated. This is determined by seeing the location of fluorescently labeled cells in the secondary channels—if correctly compensated the intensity should be the same as that of unstained cells.

EXAMPLE 5

Figure 4:
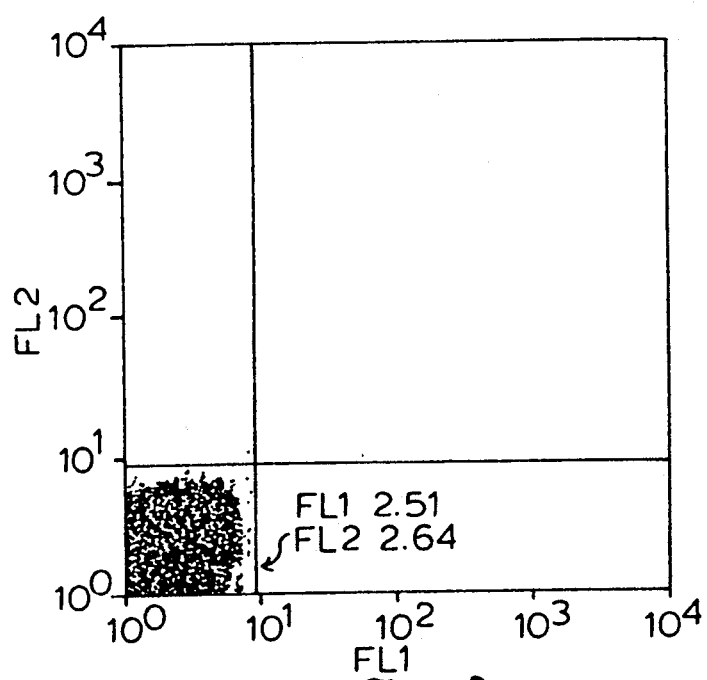
FIG. 4 is a dot plot of the green fluorescence channel FL1 versus the red fluorescence channel FL2 of CERTIFIED BLANK TM microbeads showing that their position is lower than the unstained cells in FIG. 2 (FL1 3.22 vs. 4.31 and FL2 4.60 vs. 5.390).

Demonstration that when the Pivot Point is on scale, the compensation is correct across the whole intensity range After determination of the Window of Analysis according to Example 1, CERTIFIED BLANK TM microbeads are placed in the corner of a FL1 and FL1 Window of Analysis as shown in FIG. 4. Unstained lymphocytes are found to fall at higher values in the FL1 and FL2 channels than the CERTIFIED BLANK TM microbeads because of the autofluorescence of the unstained lymphocytes. The compensation is adjusted for the mid-intensity stained CD4-FITC lymphocytes such that they have the same fluorescence in the FL2 channels as the unstained population. When the high intensity CD8-FITC stained lymphocytes are run without changing the instrument settings, they are found to be correctly compensated. When the low-intensity CD2-FITC lymphocytes are run, they are found to be correctly compensated.

EXAMPLE 6

Demonstration of use of slope in the method of the invention

Using QC3 TM microbeads, equivalent Windows of Analysis are established on a FACScan flow cytometer and a Profile II flow cytometer. The slopes determined for the instruments are 95.6 and 95.1 respectively. CD8-FITC labeled lymphocytes are run on each of the two flow cytometers and are found to be at channels 762 and 761.5, respectively, which demonstrates that is the two instruments have the same Window of Analysis.

EXAMPLE 7

Demonstration of use of Initial Target Channels vs. Instrument-Specific Target Channels to obtain comparable Window of Analysis Using a series of eleven flow cytometers, including BDIS (FACScan, FASort, FACStar Plus, FACS 440), Coulter (Profile I, Profile II) and an Ortho Cytroron, QC3 TM microbeads labeled with FITC and PE are placed in normalized Target Channels depending on the form of the reported channels (FIG. 1):

TABLE 1

| INITIAL TARGET CHANNELS | | | | |
|---|---|---|---|---|
| | 256 LC | 1024 LC | 3 Decade RLC | 4 Decade RLC |
| FL1 | 153 | 613 | 62.50 | 248.05 |
| FL2 | 170 | 679 | 97.56 | 449.10 |

Figure 2:
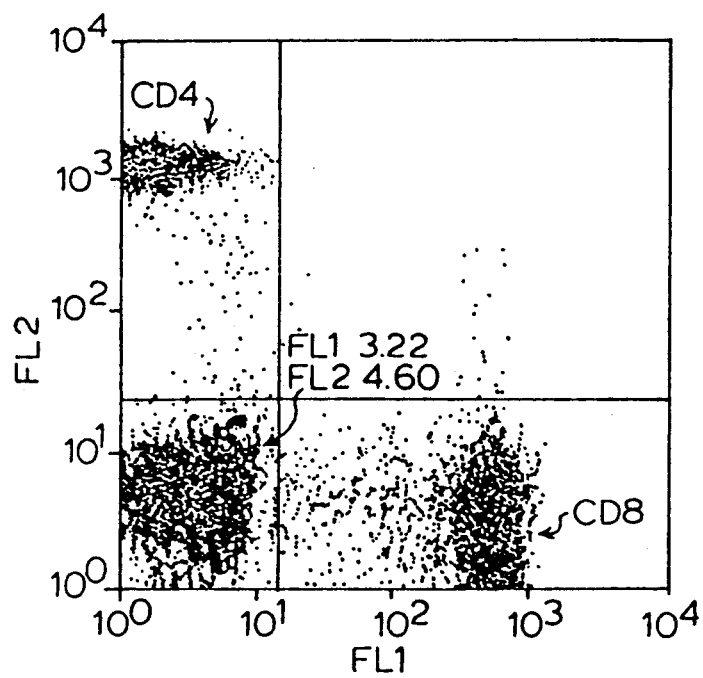
FIG. 2 is a dot plot of the green fluorescence channel FL1 versus the red fluorescence channel FL2 of gated compensated normal human lymphocytes labeled with CD8-FITC/CD4-PE monoclonal antibodies.
Figure 3:
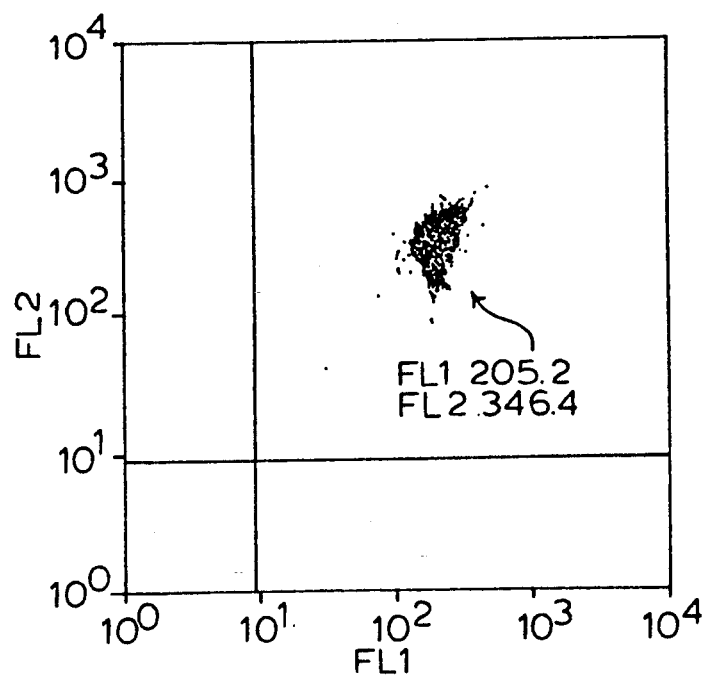
FIG. 3 is a dot plot of the green fluorescence channel FL1 versus the red fluorescence channel FL2 of QC3 TM microbeads in their Instrument Specific Target Channels after compensation (FL1 217.0 to 205.2 and FL2 438.4 to 346.4).

*LC = Linear Channels — equally spaced divisions using a log amplifier
**RLC = Relative Linear Channels — log scale divisions using a log amplifier Normal human lymphocytes labeled with CD8-FITC/CD4-PE are run on each instrument and the compensation is adjusted such that the populations are orthogonal to each other relative to the unstained population (FIG. 2). The QC3 TM microbeads are again run on each instrument and their instrument specific Target Channels are determined as the predominant channel at each wavelength FL1 and FL2 where the QC3 TM microbeads fluoresce. Examples of dot plots showing initial Target Channels and corresponding instrument-specific Target Channels are shown in FIGS. 1 and 3 respectively. A CERTIFIED BLANK TM microbead population is run on each instrument after the Instrument-Specific Target Channels are determined. The mean peak positions of the QC3 TM microbeads, CERTIFIED BLANK TM microbeads and cells are shown in Table 2:

TABLE 2

| MEAN PEAK POSITIONS | | | |
|---|---|---|---|
| Parameter | Channel | Mean | % CV |
| Initial T.C. (QC3 TM) | FL1 | 613.3 | 1.7 |
| | FL2 | 673.9 | 1.3 |
| Instrument Specific T.C. | FL1 | 608.0 | 2.2 |
| (QC3 TM) | FL2 | 654.9 | 1.8 |
| Certified Blank | FL1 | 104.4 | 98.1 |
| | FL2 | 165.9 | 91.4 |
| Unstained Lymphocytes | FL1 | 170.0 | 67.2 |
| | FL2 | 178.6 | 68.9 |
| CD8 lymphocytes | FL1 | 629.7 | 7.7 |
| | (% pos) | (25.9) | (35.8) |
| CD4 lymphocytes | FL2 | 737.4 | 8.6 |
| | (% pos) | (45.1) | (31.1) |

These data indicate that the CD8-FITC and CD4-PE cells do appear in the same position of the window of analysis and that the Target Channels can be normalized even though the instruments have different channel formats, scales and amplifier ranges.

EXAMPLE 8

Demonstration of use of blank microbeads to determine whether compensation circuits are set up correctly Using a FACstar flow cytometer (Becton Dickinson Immunocytometry Systems) with the compensation circuit turned off, a CERTIFIED BLANK ™ microbead population is run and its mean FL1 and FL2 peak channels are determined to be 2.51 and 2.64, respectively. The peak channels of unstained lymphocytes are determined to be 4.31 and 5.39 under the same instrument settings. Cells labeled with CD4-PE and CD8-FITC are run and the compensation circuits are adjusted. The CERTIFIED BLANK ™ microbeads now have peak channels at 3.29 and 4.92, whereas the unstained cells have peak channels at 3.22 and 4.60. Having the unstained cells at a lower channel than the CERTIFIED BLANK ™ microbeads with the compensation circuit turned indicates that the null voltages are not set properly. When the null voltages are set properly, the unstained cells remain at a higher channel than the CERTIFIED BLANK ™ microbeads.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of determining Target Channels for a flow cytometer having photomultiplier tubes (PMTs) with adjustable voltages, adjustable compensation circuit and a plurality of fluorescence channels, at each of at least two wavelengths such that the noise level is on scale and the compensation is uniform across the intensity ranges of the said fluorescence channels for use with fluorescent-labeled cells fluorescing at a plurality of wavelengths, comprising:
   (a) providing blank microbeads;
   (b) providing a set of control cell populations for each of said wavelengths, each control cell population being singly labeled with a fluorescent compound which fluoresces at one of said wavelengths;
   (c) providing a population of microbeads fluorescing at said wavelengths;
   (d) running the said blank microbeads on said flow cytometer and adjusting the PMT voltages so that the blank microbeads are on scale on the flow cytometer;
   (e) running said control cell populations for each said wavelengths on said flow cytometer and gating the control cell population to yield singlet cell populations;
   (f) adjusting the compensation so that the singlet cell populations fall orthogonally to unstained cells in secondary fluorescence channels; and
   (g) running said population of microbeads fluorescing at said wavelengths and determining Target Channels for the flow cytometer.

2. A method of determining Target Channels according to claim 1, wherein said fluorescent labeled cells are labeled with ein isothiocyanate and phycoerythrin.

3. A method of determining Target Channels according to claim 1, wherein said fluorescent-labeled cells are labeled with fluorescein isothiocyanate, phycoerythrin and phycoerythrin conjugated with a sulfonyl chloride derived from sulforhodamine.

4. A method of determining Target Channels according to claim 1, wherein said fluorescent-labeled cells are labeled with fluorescein isothiocyanate, phycoerythrin and phycoerythrin conjugated with a five-carbon spacer cyanine dye.

5. A method of determining Target Channels according to claim 1, wherein said fluorescent-labeled cells are labeled with fluorescein isothiocyantate, phycoerythrin and phycoerythrin conjugated with peridinin chlorophyll protein.

6. A method of setting up and subsequently maintaining a common Window of Analysis for numerous models of flow cytometers having photomultiplier tubes (PMTs) with adjustable voltages, adjustable compensation circuit and a plurality of fluorescence channels, at each of at least two wavelengths for use with fluorescent-labeled cells fluorescing at a plurality of wavelengths, comprising:
   (a) determining Initial Target Channels by:
      (i) providing blank microbeads;
      (ii) providing a set of control cell populations for each of said wavelengths, each control cell population being singly labeled with a fluorescent compound which fluoresces at one of said wavelengths;
      (iii) providing a population of microbeads fluorescing at said wavelengths;
      (iv) running said blank microbeads on said flow cytometer and adjusting the PMT voltage so that the blank microbeads are on scale on the flow cytometer;
      (v) running the control cell populations for each of said wavelengths on said flow cytometer and gating the control cell population to yield singlet cell populations;
      (vi) adjusting the compensation so that the singlet cell populations fall orthogonally to unstained cells in secondary fluorescence channels;
      (vii) turning the compensation circuit off;
      (viii) running said population of microbeads fluorescing at said wavelengths and determining Initial Target Channels for the flow cytometer; and
      (ix) calculating equivalent Initial Target Channels for flow cytometers which have different amplifiers and scales;
   (b) determining Instrument Specific Target Channels by:
      (i) running said population of microbeads fluorescing at said wavelengths with the compensation off and adjusting the PMT collages to place the fluorescing microbeads in said Initial Target Channels;
      (ii) running the control cell populations for each of said wavelengths on said flow cytometer and gating the control cell population to yield singlet cell populations;
      (iii) adjusting the compensation so that the singlet cell populations fall orthogonally to unstained cells in secondary fluorescence channels; and
      (iv) running said population of microbeads fluorescing at said wavelengths and determining the Instrument Specific Target Channels; and
   (c) subsequently using the Instrument Specific Target Channels by:

(i) adjusting PMT and compensation settings to those determined in section (b);

(ii) running said population of microbeads fluorescing at said wavelengths and determining if said microbeads fall in said Instrument Specific Target Channels and thus if said instrument is performing as determined previously;

(iii) running the control cell populations for each of said wavelengths on said flow cytometer, gating the control cell population, and determining if the singlet cell populations fall in the same positions as previously and thus indicating said cells, or reagents or preparation are unchanged; and (iv) running said blank microbeads on said flow cytometer and determining if the blank microbeads have a lower fluorescence than the unstained cells and thus that the flow cytometer noise level will not interfere with assay.

7. A method of setting up and subsequently maintaining a common Window of Analysis according to claim 6-, wherein said fluorescent labeled cells are labeled with fluorescein isothiocyanate and phycoerythrin.

8. A method of setting up and subsequently maintaining a common Window of Analysis according to claim 6, wherein said fluorescent-labeled cells are labeled with fluorescein isothiocyanate, phycoerythrin and phycoerythrin conjugated with a sulfonyl chloride derived from sulforhodamine.

9. A method of setting up and subsequently maintaining a common Window of Analysis according to claim 6, wherein said fluorescent-labeled cells are labeled with fluorescein isothiocyanate, phycoerythrin and phycoerythrin conjugated with a five-carbon spacer cyanine dye.

10. A method of setting up and subsequently maintaining a common Window of Analysis according to claim 6, wherein said fluorescent-labeled cells are labeled with fluorescein isothiocyanate, phycoerythrin and phycoerythrin conjugated with peridinin chlorophyll protein.

11. A method of determining whether compensation circuits of a flow cytometer have been correctly set up, said flow cytometer having photomultiplier tubes (PMTs) with adjustable voltages, adjustable compensation circuits and a plurality of fluorescence channels, at each of at least two wavelengths for use with fluorescent cells for use with selected cells being fluorescently labeled to fluoresce at a plurality of wavelengths, comprising:

(a) turning said compensation circuits off;

(b) running blank microbeads on said flow cytometer and determining peak channels for said blank microbeads in said fluorescence channels;

(c) running unstained cells on said flow cytometer and determining peak channels for said unstained cells in said fluorescence channels;

(d) determining whether there is a lower fluorescence intensity for the blank microbeads than the unstained cells and therefore that flow cytometer noise will not interfere with a cell assay;

(e) turn said compensation circuits on;

(f) running blank microbeads on said flow cytometer and determining peak channels for said blank microbreads in said fluorescence channels;

(g) running unstained cells on said flow cytometer and determining peak channels for said unstained cells in said fluorescence channels; and (h) determining whether said blank microbeads have a higher fluorescence intensity than the unstained cells, and therefore that the compensation circuit requires adjustment.

* * * * *